United States Patent
Vuong et al.

(10) Patent No.: US 7,505,148 B2
(45) Date of Patent: Mar. 17, 2009

(54) MATCHING OPTICAL METROLOGY TOOLS USING SPECTRA ENHANCEMENT

(75) Inventors: Vi Vuong, Fremont, CA (US); Yan Chen, Santa Clara, CA (US); Holger Tuitje, Fremont, CA (US)

(73) Assignee: Tokyo Electron Limited, Tokyo (JP)

( * ) Notice: Subject to any disclaimer, the term of this patent is extended or adjusted under 35 U.S.C. 154(b) by 190 days.

(21) Appl. No.: 11/601,351

(22) Filed: Nov. 16, 2006

(65) Prior Publication Data

US 2008/0117411 A1    May 22, 2008

(51) Int. Cl.
 *G01N 21/00* (2006.01)
(52) U.S. Cl. .................. 356/601; 356/614; 356/625
(58) Field of Classification Search .................. 356/601, 356/625, 636–640, 237.2, 237.5; 250/559.22, 250/559.24, 550; 700/108, 121, 95–96; 702/97, 702/189; 438/14, 16
See application file for complete search history.

(56) References Cited

U.S. PATENT DOCUMENTS

| | | | |
|---|---|---|---|
| 6,532,428 B1 * | 3/2003 | Toprac | 702/97 |
| 6,645,824 B1 * | 11/2003 | Yang et al. | 438/401 |
| 6,785,638 B2 | 8/2004 | Niu et al. | |
| 6,791,680 B1 * | 9/2004 | Rosengaus et al. | 356/237.2 |
| 6,792,328 B2 * | 9/2004 | Laughery et al. | 700/121 |
| 6,891,626 B2 | 5/2005 | Niu et al. | |
| 6,943,900 B2 | 9/2005 | Niu et al. | |
| 7,352,453 B2 * | 4/2008 | Mieher et al. | 356/125 |
| 7,395,132 B2 * | 7/2008 | Prager et al. | 700/108 |
| 2004/0267397 A1 | 12/2004 | Doddi et al. | |

OTHER PUBLICATIONS

Ausschnitt, C. P. (Feb. 23, 2004). "A New Approach to Pattern Metrology," *Proceedings of SPIE* 5375:51-65.
U.S. Appl. No. 11/371,752, filed Mar. 8, 2006 for Vuong et al.

\* cited by examiner

*Primary Examiner*—Sang Nguyen
(74) *Attorney, Agent, or Firm*—Morrison & Foerster LLP

(57) ABSTRACT

Optical metrology tools are matched by obtaining a first set of measured diffraction signals, which was measured using a first optical metrology tool, and a second set of measured diffraction signals, which was measured using a second optical metrology tool. A first spectra-shift offset is generated based on the difference between the first set of measured diffraction signals and the second set of measured diffraction signals. A first noise weighting function for the first optical metrology tool is generated based on measured diffraction signals measured using the first optical metrology tool. A first measured diffraction signal measured using the first optical metrology tool is obtained. A first adjusted diffraction signal is generated by adjusting the first measured diffraction signal using the first spectra-shift offset and the first noise weighting function.

37 Claims, 6 Drawing Sheets

MATCHING OPTICAL METROLOGY TOOLS USING SPECTRA ENHANCEMENT

BACKGROUND

1. Field

The present application relates to optical metrology, and, more particularly, to matching optical metrology tools using spectra enhancement.

2. Related Art

Optical metrology involves directing an incident beam at a structure, measuring the resulting diffracted beam, and analyzing the diffracted beam to determine a feature of the structure. In semiconductor manufacturing, optical metrology is typically used for quality assurance. For example, after fabricating a structure on a semi-conductor wafer an optical metrology tool is used to determine the profile of the structure. By determining the profile of the structure, the quality of the fabrication process utilized to form the structure can be evaluated.

As a result of the broad adoption of optical metrology, one fabrication facility or site where microelectronics are manufactured typically has multiple optical metrology tools in a fleet whose results are used somewhat interchangeably. In these cases, it is desirable that the instruments in the fleet match one another. In the ideal case, if the instruments were identical, their measurements would match to some uncertainty determined by measurement noise. However, optical metrology tools show deterministic differences, where the difference between the measurements is greater than the uncertainties of the measurement. One approach to improve matching is to carefully calibrate the tools, so that the optical characteristics measured by tools are as similar as possible, even if the details of each of the tools construction dictate that the detected intensities on the same sample are different. In some sense, this is the goal of calibration.

Calibration is typically done with calibration structures, with the intention that the calibration will remain valid for measurements on various application structures. Often calibration structures are one or more thicknesses of an oxide on a silicon substrate. Application structures can be very different than these simple calibration structures. In a fabrication facility, one application structure can be resist on top of a stack of layers for the formation of transistor gates after it has been exposed and developed, in order to examine the effects of adjusting, e.g., focus and dose on the exposure tool. Another application structure can be shallow isolation trenches in a silicon substrate. In general, the optical characteristics of these application structures can be substantially different from one another, and from the optical characteristics employed in calibration, which is ideally intended to be valid for all structures.

However, even after the optical metrology tools in a fleet have been calibrated, their optical characteristics, and subsequently their fit parameters, can differ. Such differences can be an issue for the control of processes in the fabrication facility. Accordingly, it is desirable to compensate for variations in the optical characteristics of optical metrology tools for a given application.

SUMMARY

In one exemplary embodiment, optical metrology tools are matched by obtaining a first set of measured diffraction signals, which was measured using a first optical metrology tool, and a second set of measured diffraction signals, which was measured using a second optical metrology tool. A first spectra-shift offset is generated based on the difference between the first set of measured diffraction signals and the second set of measured diffraction signals. A first noise weighting function for the first optical metrology tool is generated based on measured diffraction signals measured using the first optical metrology tool. A first measured diffraction signal measured using the first optical metrology tool is obtained. A first adjusted diffraction signal is generated by adjusting the first measured diffraction signal using the first spectra-shift offset and the first noise weighting function.

DESCRIPTION OF DRAWING FIGURES

The present application can be best understood by reference to the following description taken in conjunction with the accompanying drawing figures, in which like parts may be referred to by like numerals:

DETAILED DESCRIPTION

The following description sets forth numerous specific configurations, parameters, and the like. It should be recognized, however, that such description is not intended as a limitation on the scope of the present invention, but is instead provided as a description of exemplary embodiments.

1. Optical Metrology Tools

Figure 1:
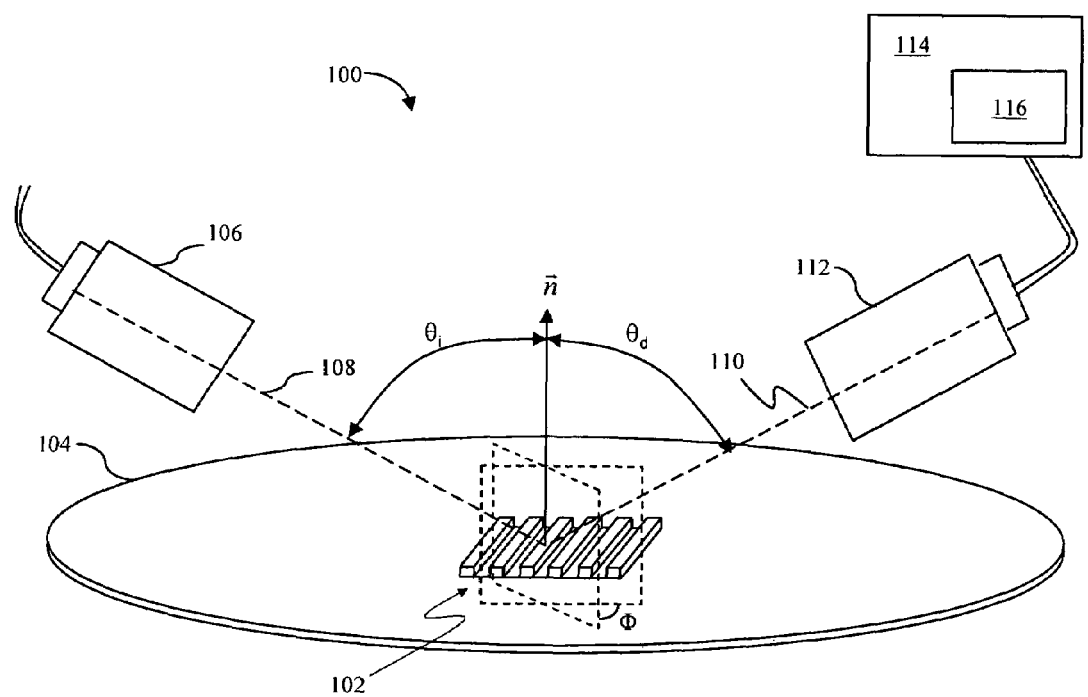
FIG. 1 depicts an exemplary optical metrology system.

With reference to FIG. 1, an optical metrology system 100 can be used to examine and analyze a structure formed on a semiconductor wafer 104. For example, optical metrology system 100 can be used to determine one or more features of a periodic grating 102 formed on wafer 104. As described earlier, periodic grating 102 can be formed in a test pad on wafer 104, such as adjacent to a die formed on wafer 104. Periodic grating 102 can be formed in a scribe line and/or an area of the die that does not interfere with the operation of the die.

As depicted in FIG. 1, optical metrology system 100 can include a photometric device with a source 106 and a detector 112. Periodic grating 102 is illuminated by an incident beam 108 from source 106. The incident beam 108 is directed onto periodic grating 102 at an angle of incidence $\theta_i$ with respect to normal $\vec{n}$ of periodic grating 102 and an azimuth angle $\Phi$ (i.e., the angle between the plane of incidence beam 108 and the direction of the periodicity of periodic grating 102). Diffracted beam 110 leaves at an angle of $\theta_d$ with respect to normal and is received by detector 112. Detector 112 converts the diffracted beam 110 into a measured diffraction signal, which can include reflectance, tan ($\Psi$), cos($\Delta$), Fourier coefficients, and the like. Although a zero-order diffraction signal is depicted in FIG. 1, it should be recognized that non-zero orders can also be used. For example, see Ausschnitt, Christopher P., "A New Approach to Pattern Metrology," Proc. SPIE 5375-7, Feb. 23, 2004, pp 1-15, which is incorporated herein by reference in its entirety.

Optical metrology system 100 also includes a processing module 114 configured to receive the measured diffraction signal and analyze the measured diffraction signal. The processing module is configured to determine one or more features of the periodic grating using any number of methods which provide a best matching diffraction signal to the measured diffraction signal. These methods can include a library-based process, or a regression based process using simulated diffraction signals obtained by rigorous coupled wave analysis and machine learning systems. See, U.S. Pat. No. 6,943,900, titled GENERATION OF A LIBRARY OF PERIODIC GRATING DIFFRACTION SIGNALS, filed on Jul. 16, 2001, issued Sep. 13, 2005, which is incorporated herein by reference in its entirety; U.S. Pat. No. 6,785,638, titled METHOD AND SYSTEM OF DYNAMIC LEARNING THROUGH A REGRESSION-BASED LIBRARY GENERATION PROCESS, filed on Aug. 6, 2001, issued Aug. 31, 2004, which is incorporated herein by reference in its entirety; U.S. Pat. No. 6,891,626, titled CACHING OF INTRA-LAYER CALCULATIONS FOR RAPID RIGROUS COUPLED-WAVE ANALYSES, filed on Jan. 25, 2001, issued May 10, 2005, which is incorporated herein by reference in its entirety; and U.S. patent application Ser. No. 10/608,300, titled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety.

2. Matching Optical Metrology Tools

As described above, optical metrology tools in a fleet can be calibrated. However, even after calibration, variations in optical characteristics of the optical metrology tools in the fleet can produce variations in the results obtained using the optical metrology tools. Thus, in one exemplary embodiment, the optical metrology tools in the fleet are matched using spectra enhancement.

Figure 2:
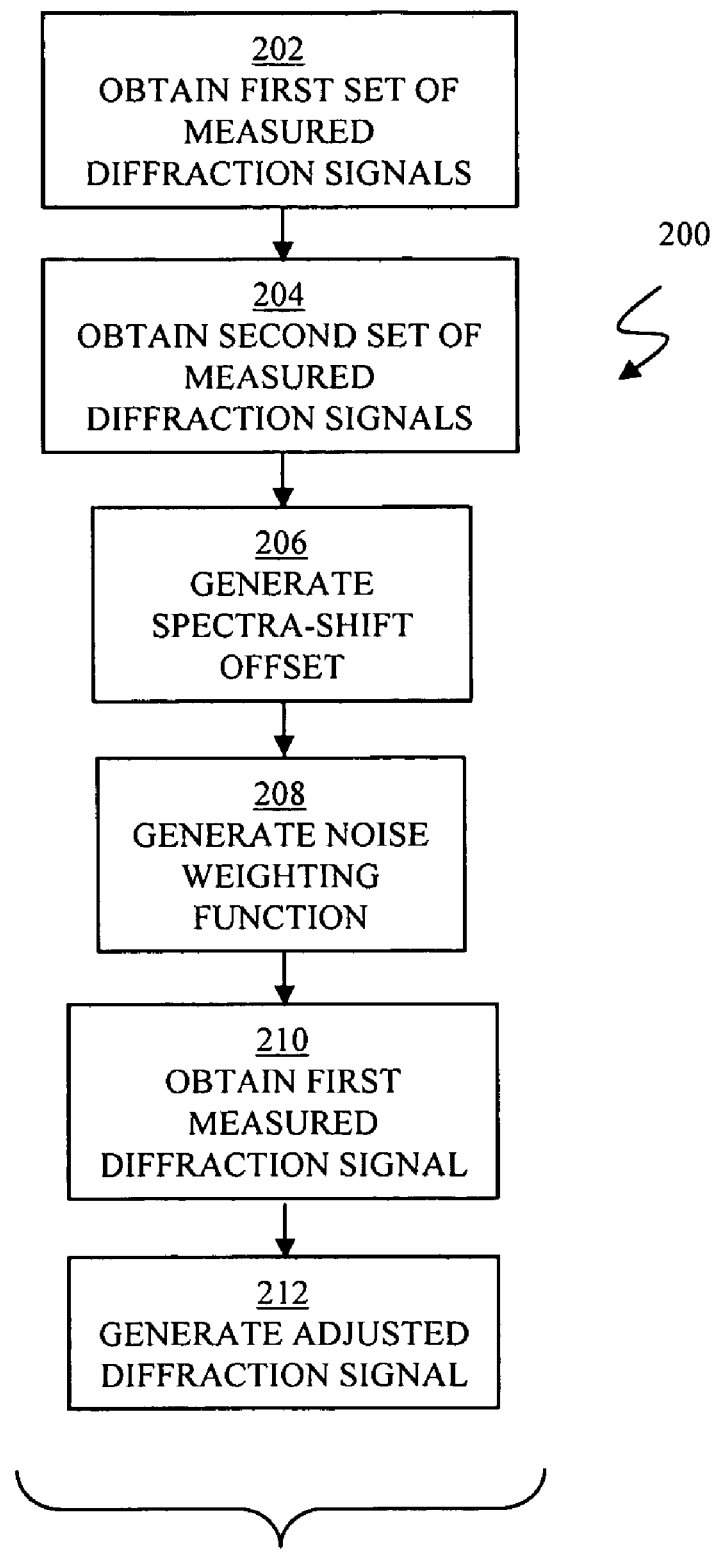
FIG. 2 depicts an exemplary process of matching optical metrology tools.

In particular, with reference to FIG. 2, an exemplary process 200 is depicted of matching optical metrology tools in a fleet of optical metrology tools using spectra enhancement. In step 202, a first set of measured diffraction signals is obtained. The first set of measured diffraction signals is measured using a first optical metrology tool in the fleet. In step 204, a second set of measured diffraction signals is obtained. The second set of measured diffraction signals is measured using a second optical metrology tool in the fleet.

Figure 3:
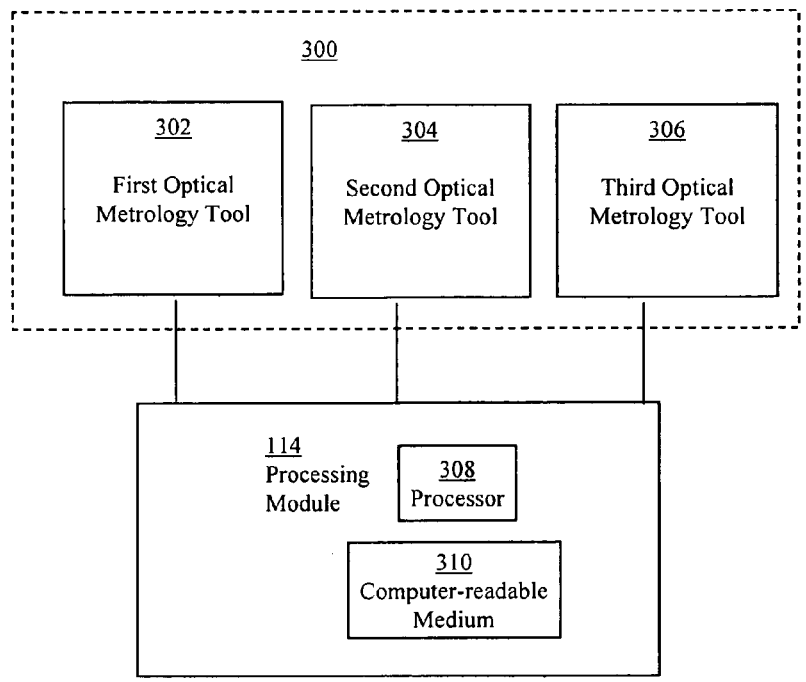
FIG. 3 depicts an exemplary fleet of optical metrology tools.

For example, FIG. 3 depicts an exemplary fleet 300 having a first optical metrology tool 302 and a second optical metrology tool 304. The first and second optical metrology tools 302, 304 can be reflectometers, ellipsometers, and the like. A first set of measured diffraction signals is measured using first optical metrology tool 302. A second set of measured diffraction signals is measured using second optical metrology tool 304. As also depicted in FIG. 3, processing module 114 can obtain the first and second sets of measured diffraction signals measured using first optical metrology tool 302 and second optical metrology tool 304, respectively.

It should be recognized that fleet 300 can include any number of optical metrology tools, and any number of sets of measured diffraction signals can be obtained from any number of optical metrology tools. As an example, fleet 300 is depicted having a third optical metrology tool 306, which can be used to measure a third set of measured diffraction signals.

With reference to FIG. 2, in step 206, a spectra-shift offset is generated based on the difference between the first set of measured diffraction signals and the second set of measured diffraction signals. In the present exemplary embodiment, the first set of measured diffraction signals was measured from a set of sites on a wafer, and the second set of measured diffraction signals was measured from the same set of sites on the same wafer as the first set of measured diffraction signals. For example, with reference again to FIG. 3, a set of sites on a wafer can be measured using first optical metrology tool 302, then the same set of sites on the same wafer can be measured using second optical metrology tool 304. In the present exemplary embodiment, the spectra-shift offset is calculated as the average of the differences between each measured diffraction signal in the first set of measured diffraction signal and each measured diffraction signal in the second set of measured diffraction signals measured from the same site on the same wafer.

Figure 4:
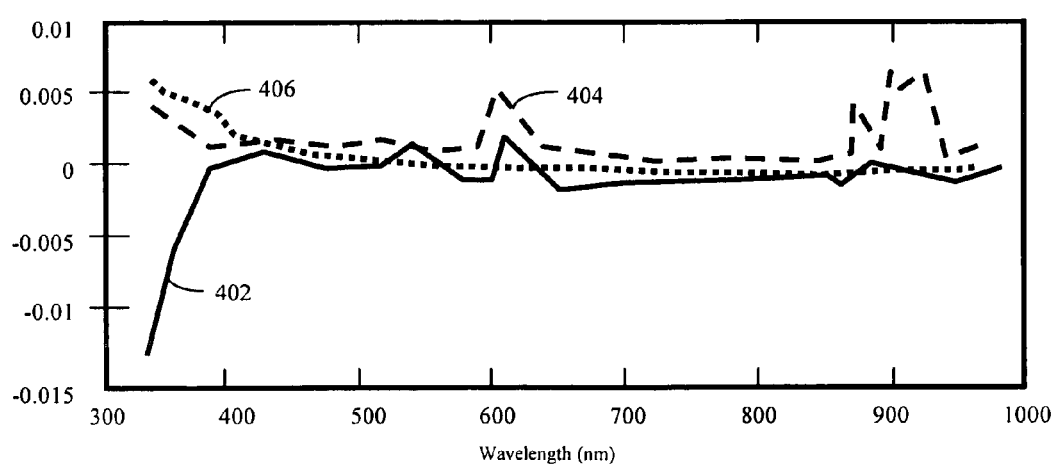
FIG. 4 depict exemplary graphs of spectra-shift offset, noise weighting function, and default noise function.

The spectra-shift offset can be a vector, a table, or graph. For example, FIG. 4 depicts an exemplary spectra-shift offset depicted as a graph 402. As depicted in FIG. 4, graph 402 provides the average of the spectra differences between the first and second sets of measured diffraction signals over the wavelengths used in obtaining the first and second sets of measured diffraction signals. It should be recognized that any range of wavelengths can be used. See, U.S. Pat. No. 6,792,328, titled METROLOGY DIFFRACTION SIGNAL ADAPTATION FOR TOOL-TO-TOOL MATCHING, filed on Mar. 29, 2002, and issued on Sep. 14, 2004, which is incorporated herein by reference in its entirety.

With reference again to FIG. 3, as mentioned above, fleet 300 can include any number of optical metrology tools. In the present exemplary embodiment, the spectra-shift offset is determined between any one of the optical metrology tools in fleet 300 and a reference optical metrology tool, which can be one of the optical metrology tools in fleet 300 or a separate optical metrology tool. For the sake of the present example, assume second optical metrology tool 304 is the reference optical metrology tool. Thus, the spectra-shift offset for third optical metrology tool 306 is generated based on the difference between the second set of measured diffraction signals measured using second optical metrology tool 304 and the third set of measured diffraction signals measured using third optical metrology tool 306.

With reference again to FIG. 2, in step 208, a noise weighting function is generated for the first optical metrology tool based on measured diffraction signals measured using the first optical metrology tool. In particular, the noise weighting function is defined based on the noise that exists in obtaining the measured diffraction signal using the first optical metrology tool. The noise can be related to the hardware used to obtain the measured diffraction signal, such as the optics and electronics used in the first optical metrology tool. The noise can also be related to the feature being measured, such as the phenomenon of resist bleaching resulting from the source.

Figure 5:
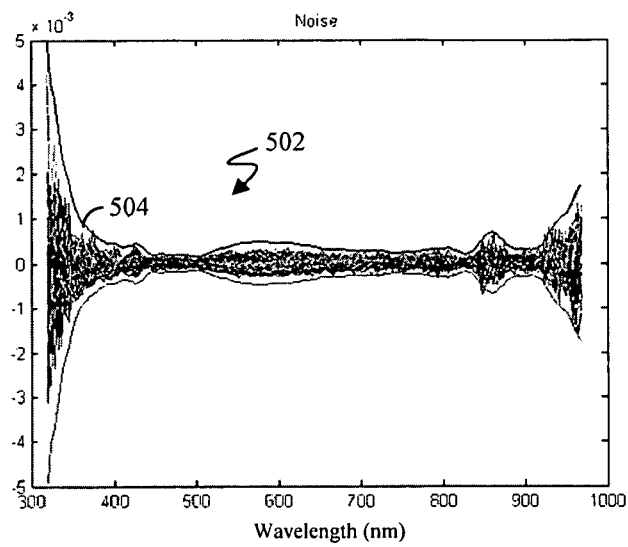
FIG. 5 depicts an exemplary noise profile.

With reference to FIG. 5, in the present exemplary embodiment, to define a noise weighting function, a noise profile 502 is first generated. In particular, a set of measured diffraction signals are obtained. The set of measured diffraction signals can be obtained in advance from a single site on a wafer using the first optical metrology tool. Note, the site from which the set of measured diffraction signal are obtained can be on a different wafer than the wafer on which the feature to be examined is formed.

An average measured diffraction signal is calculated from the set of measured diffraction signals. Noise profile 502 is the difference between each of the measured diffraction signals and the average measured diffraction signal. Noise profile 502 depicted in FIG. 5 was calculated from 50 measured diffraction signals. It should be recognized, however, that any number of measured diffraction signals can be obtained to generate a noise profile. Because noise profile 502 is generated from measured diffraction signals, noise profile 502 takes into account noise resulting from both hardware related noise and feature related noise.

After noise profile 502 is obtained, a noise envelope 504 is defined based on noise profile 502. In the present exemplary embodiment, noise envelope 504 is defined using maximum values of noise profile 502 and a curve smoothing technique. It should be recognized, however, that noise envelope 504 can be defined using various numerical techniques.

Figure 6:
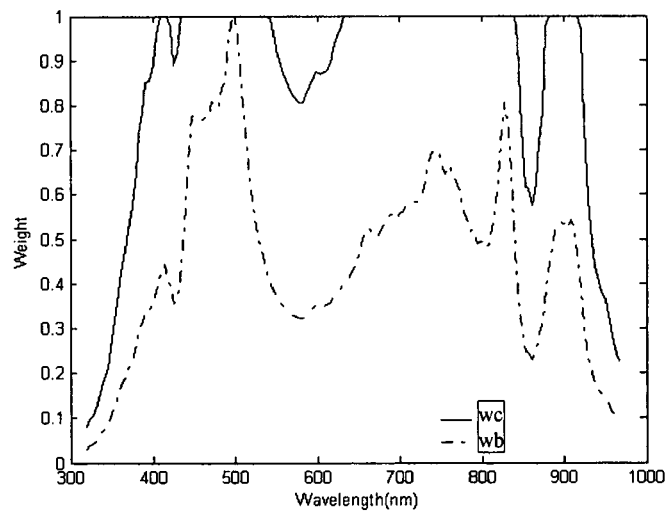
FIG. 6 depicts exemplary noise weighting functions.

With reference to FIG. 6, in the present exemplary embodiment, a noise weighting function wb is defined by inverting noise envelope 504 (FIG. 5). Noise weighting function wb can be modified to generate additional weighting functions. For example, noise weighting function wc is generated by scaling and truncating noise weighting function wb.

Figure 7:
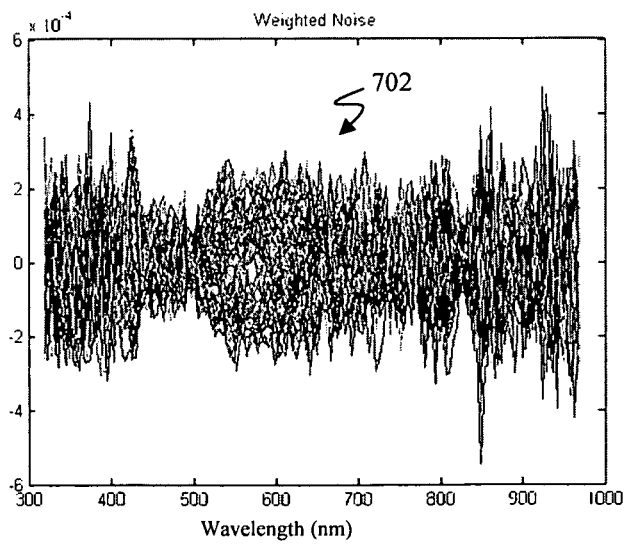
FIG. 7 depicts another exemplary noise profile.

FIG. 7 depicts a noise profile 702 generated by enhancing noise profile 502 (FIG. 5) using noise weighting function wc (FIG. 6). In particular, noise profile 502 (FIG. 5) is multiplied by noise weighting function wc (FIG. 6) to generate noise profile 702. As depicted in FIG. 7, noise weighting function wc reduces the amount of noise and increases the uniformity of noise profile 702. Note, however, that noise weighting function wc does not entirely eliminate noise. Completely eliminating noise can degrade the measured diffraction signal, which can reduce accuracy of the optical metrology process.

Thus, in the present exemplary embodiment, the noise weighting function is modified to remove the desired amount of noise from the measured diffraction signal without overly degrading the measured diffraction signal. Additionally, the noise weighting function can be modified to shape the amount of noise reduction of a measured diffraction signal. For example, the noise weighting function can be modified to reduce less noise at one portion of a measured diffraction signal compared to another portion of the measured diffraction signal.

With reference again to FIG. 4, an exemplary noise weighting function 404 is depicted as a graph. FIG. 4 also depicts an exemplary default noise function 406, which can be determined empirically, simulated, or derived based upon experience. Noise weighting function 404 and default noise function 406 are depicted over the range of wavelengths used in obtaining the first and second sets of measured diffraction signal. It should be recognized that any range of wavelengths can be used. See, U.S. patent application Ser. No. 11/371,752, titled WEIGHTING FUNCTION TO ENHANCE MEASURED DIFFRACTION SIGNALS IN OPTICAL METROLOGY, filed on Mar. 8, 2006, which is incorporated herein by reference in its entirety.

With reference again to FIG. 2, in step 210, a measured diffraction signal is obtained. The measured diffraction signal is measured using the first optical metrology tool. In step 212, an adjusted diffraction signal is generated by adjusting the measured diffraction signal measured using the first optical metrology tool using the first spectra-shift offset and the noise weighting function. It should be recognized that the first spectra-shift offset and the noise weighting function can be applied in any order to the measured diffraction signal to generate the adjusted diffraction signal.

With reference again to FIG. 3, as mentioned above, fleet 300 can include any number of optical metrology tools. In the present exemplary embodiment, the noise weighting function is generated and the adjusted diffraction signal is generated for any one of the optical metrology tools in fleet 300. For the sake of the present example, a noise weighting function is generated for third metrology tool 306 in the same manner as the noise weighting function was generated for second metrology tool 304. As described above, a spectra-shift offset for third optical metrology tool 306 is generated based on the difference between the second set of measured diffraction signals measured using second optical metrology tool 304 and the third set of measured diffraction signals measured using third optical metrology tool 306. A measured diffraction signal is measured using third metrology tool 306, then an adjusted diffraction signal is generated by adjusting the measured diffraction signal measured using the third optical metrology tool using the spectra-shift offset and the noise weighting function for the third optical metrology tool.

3. Generating a Drift Function

Even after calibration, the measurements obtained using an optical metrology tool may drift over time. Thus, in one exemplary embodiment, a drift function is generated and used to compensate for drift.

Figure 8:
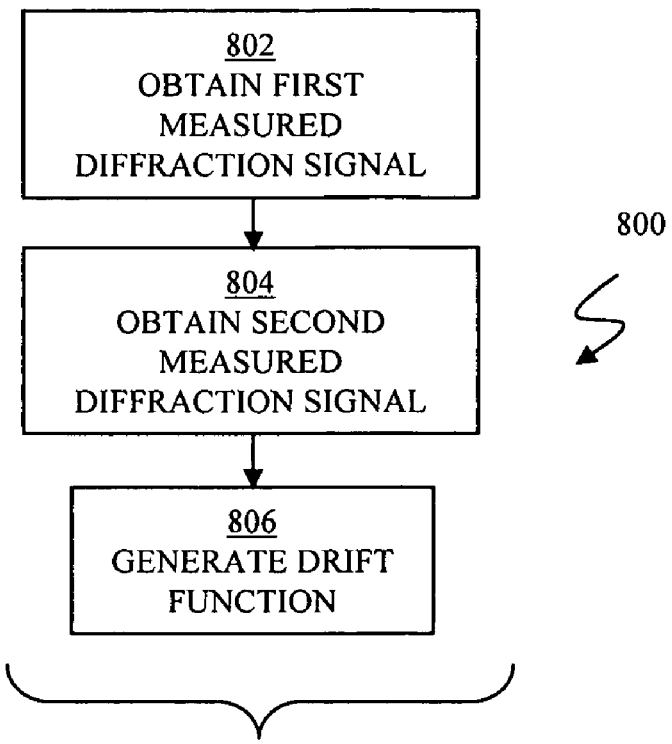
FIG. 8 depicts an exemplary process of generating a shift function.

In particular, with reference to FIG. 8, an exemplary process 800 is depicted of generating a drift function used to compensate for drift in an optical metrology tool. In step 802, a first measured diffraction signal is obtained of a calibration structure mounted on the first optical metrology tool. In step 804, a second measured diffraction signal is obtained of the calibration structure mounted on the first optical metrology tool. The first and second measured diffraction signals were measured of the calibration structure using the first optical metrology tool. The second measured diffraction signal is measured later in time than the first measured diffraction signal. In step 806, a drift function is generated based on the difference between the second measured diffraction signal and the first measured diffraction signal.

In one exemplary embodiment, after generating the drift function, a measured diffraction signal measured using the first optical metrology tool is adjusted using the drift function. Thus, in this manner, the drift in the first optical metrology tool is compensated using the drift function. In another exemplary embodiment, the drift function is applied along with the spectra-shift and the noise weighting function to generate the adjusted diffraction signal mentioned above.

Figure 9:
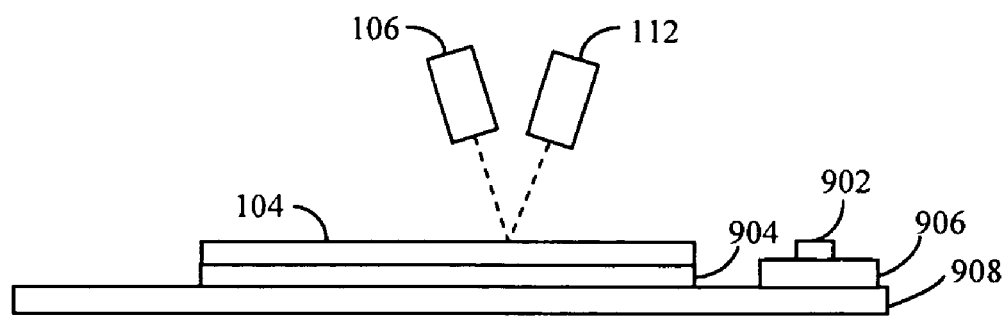
FIG. 9 depicts an exemplary calibration structure mounted on an optical metrology tool.

With reference now to FIG. 9, an exemplary calibration structure 902 is depicted. As described above, in one exemplary embodiment, calibration structure 902 is mounted on an optical metrology tool. In the exemplary embodiment depicted in FIG. 9, calibration structure 902 is depicted mounted on a wafer stage 908 of an optical metrology tool. Calibration structure 902 is mounted on a support 906 such that the surface of calibration structure is substantially in the same plane as the surface of wafer 104. As also depicted in FIG. 9, wafer 104 is held by wafer chuck 904. The optical metrology device also includes a source 106 and detector 112. As described above, source 106 directs an incident beam at a structure to be examined, and detector 112 receives the diffracted beam. In the present exemplary embodiment, source 106 and detector 112 are used to measure calibration structure 902 over periods of time to generate the drift function as described above.

Figure 10:
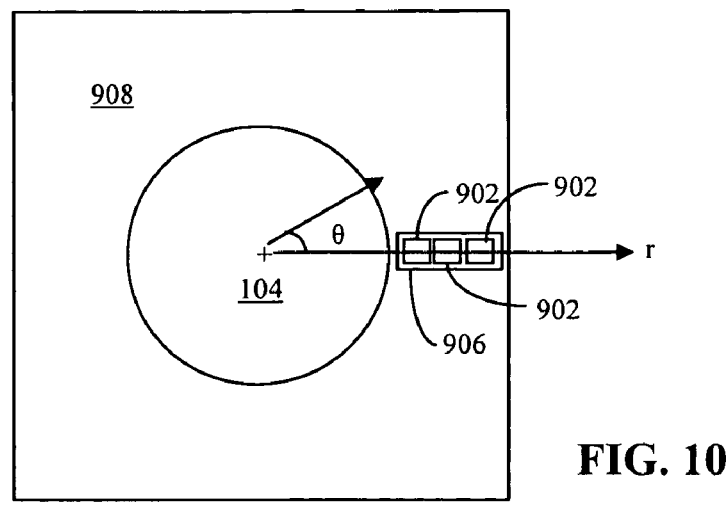
FIG. 10 depicts exemplary calibration structures mounted on an optical metrology tool with an r-theta stage.
Figure 11:
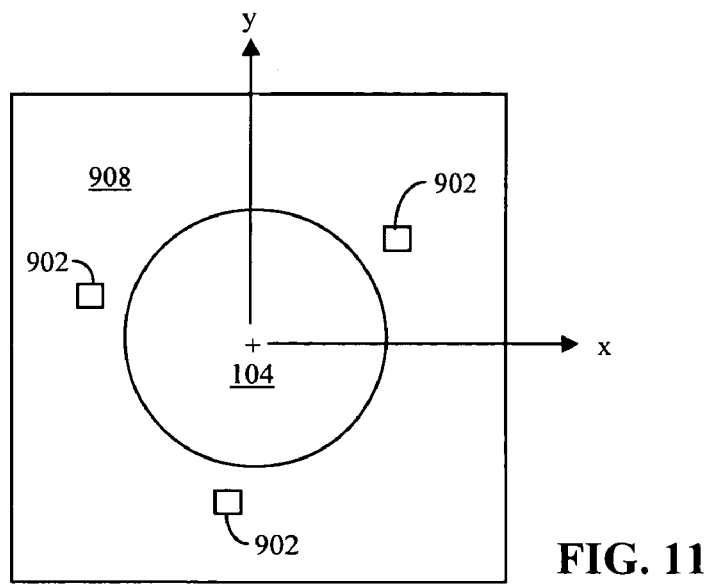
FIG. 11 depicts exemplary calibration structures mounted on an optical metrology tool with an x-y stage.

In one exemplary embodiment, multiple calibration structures 902 can be mounted on an optical metrology tool. Each calibration structure 902 can be used for different applications. With reference to FIG. 10, in an optical metrology device with an R-theta stage 908, which moves wafer 104 relative to source 106 and/or detector 112 in an r (radial) direction and an angle theta direction, as indicated in FIG. 10, the multiple calibration structures 902 can be mounted in-line along a radial direction on support 906. With reference to FIG. 11, in an optical metrology device with an X-Y stage 908, which moves wafer 104 relative to source 106 and/or detector 112 in an x direction and y direction, as indicated in FIG. 11, the multiple calibration structures 902 can be distributed radially around where wafer 104 is held in wafer chuck 904 (FIG. 9).

With reference to FIG. 10, multiple calibration structures 902 can be mounted in support 906, such as a bracket. Each calibration structure 902 can be a chip with one or more grating structures. Multiple chips can be formed on a single wafer, diced and used as calibration structures 902 on one or more optical metrology tools.

Figure 12:
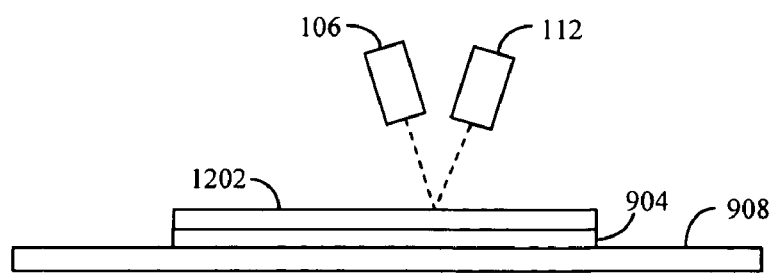
FIG. 12 depicts an exemplary calibration wafer.

With reference to FIG. 12, in another exemplary embodiment, a calibration wafer 1202 is used to generate a drift function rather than calibration structures. Similar to the process described for calibration structures, calibration wafer 1202 is measured periodically, and a drift function is generated based on the difference between two measured diffraction signals measured from the same site on calibration wafer 1202 at two different times.

Calibration wafer 1202 may have several calibration structures formed in selected sites in several sections or sectors. These calibration structures may be measured and the statistical average of the differences between two measured diffraction signals may be used in generating the drift function. For integrated metrology, where a metrology tool is integrated with one or more fabrication tools, one or more calibration wafers 1202 may be included in the lot of wafers measured in a periodic basis in the metrology tool of a fabrication cluster. With a history of how the drift function has changed over time or a function of some other variable, such as the number of wafer lots processed, a predictive model of the drift function may be developed. The predictive model may be used instead of physically measuring the calibration structures or calibration wafer 1202.

Although exemplary embodiments have been described, various modifications can be made without departing from the spirit and/or scope of the present invention. Therefore, the present invention should not be construed as being limited to the specific forms shown in the drawings and described above.

We claim:

1. A method of matching optical metrology tools, the method comprising:
   obtaining a first set of measured diffraction signals, wherein the first set of measured diffraction signals was measured using a first optical metrology tool;
   obtaining a second set of measured diffraction signals, wherein the second set of measured diffraction signals was measured using a second optical metrology tool;
   generating a first spectra-shift offset based on the difference between the first set of measured diffraction signals and the second set of measured diffraction signals;
   generating a first noise weighting function for the first optical metrology tool based on measured diffraction signals measured using the first optical metrology tool;
   obtaining a first measured diffraction signal measured using the first optical metrology tool;
   generating a first adjusted diffraction signal by adjusting the first measured diffraction signal using the first spectra-shift offset and the first noise weighting function; and
   storing the first adjusted diffraction signal.

2. The method of claim 1, further comprising:
   obtaining a third set of measured diffraction signals, wherein the third set of measured diffraction signals was measured using a third optical metrology tool;
   generating a second spectra-shift offset based on the difference between the third set of measured diffraction signals and the second set of measured diffraction signals;
   generating a second noise weighting function for the third optical metrology tool based on measured diffraction signals measured using the third optical metrology tool;
   obtaining a second measured diffraction signal measured using the third optical metrology tool; and
   generating a second adjusted diffraction signal by adjusting the second measured diffraction signal using the second spectra-shift offset and the second noise weighting function.

3. The method of claim 1, wherein the first spectra-shift offset is a vector, table, or graph.

4. The method of claim 1, wherein the first set of measured diffraction signals was measured from a set of sites on a wafer, wherein the second set of measured diffraction signals was measured from the same set of sites on the same wafer as the first set of measured diffraction signals.

5. The method of claim 4, wherein generating a first spectra-shift offset comprises:
   calculating differences between each measured diffraction signal in the first set of measured diffraction signals and each measured diffraction signal in the second set of measured diffraction signals measured from the same site on the same wafer.

6. The method of claim 1, wherein generating a first noise weighting function comprises:
   generating a noise profile based on the measured diffraction signals measured using the first optical metrology tool;
   defining a noise envelope based on the noise profile; and
   defining the first noise weighting function based on the noise envelope.

7. The method of claim 6, wherein the measured diffraction signals measured using the first optical metrology tool are the same or a subset of the first set of measured diffraction signals.

8. The method of claim 6, wherein the measured diffraction signals measured using the first optical metrology tool are different than the first set of measured diffraction signals.

9. The method of claim 1, further comprising:
   obtaining a measurement of a calibration structure mounted on the first optical metrology tool using the first optical metrology tool;
   generating a drift function based on the obtained measurement of the calibration structure; and
   generating the first adjusted diffraction signal by adjusting the first measured diffraction signal using the drift function.

10. The method of claim 9, wherein generating the drift function comprises:
    comparing the obtained measurement of the calibration structure to a previous measurement of the calibration structure measured using the first optical metrology tool.

11. The method of claim 9, wherein the calibration structure is a chip mounted on a wafer stage.

12. The method of claim 11, wherein the chip includes a grating structure.

13. The method of claim 9, wherein the calibration structure includes a plurality of calibration structures, wherein each calibration structure is different, and the different calibration structures are measured for different applications.

14. A computer-readable storage medium having computer executable instructions for matching optical metrology tools, comprising instructions for:
obtaining a first set of measured diffraction signals, wherein the first set of measured diffraction signals was measured using a first optical metrology tool;
obtaining a second set of measured diffraction signals, wherein the second set of measured diffraction signals was measured using a second optical metrology tool;
generating a first spectra-shift offset based on the difference between the first set of measured diffraction signals and the second set of measured diffraction signals;
generating a first noise weighting function for the first optical metrology tool based on measured diffraction signals measured using the first optical metrology tool;
obtaining a first measured diffraction signal measured using the first optical metrology tool;
generating a first adjusted diffraction signal by adjusting the first measured diffraction signal using the first spectra-shift offset and the first noise weighting function; and
storing the first adjusted diffraction signal.

15. The computer-readable storage medium of claim 14, further comprising instructions for:
obtaining a third set of measured diffraction signals, wherein the third set of measured diffraction signals was measured using a third optical metrology tool;
generating a second spectra-shift offset based on the difference between the third set of measured diffraction signals and the second set of measured diffraction signals;
generating a second noise weighting function for the third optical metrology tool based on measured diffraction signals measured using the third optical metrology tool;
obtaining a second measured diffraction signal measured using the third optical metrology tool; and
generating a second adjusted diffraction signal by adjusting the second measured diffraction signal using the second spectra-shift offset and the second noise weighting function.

16. The computer-readable storage medium of claim 14, further comprising instructions for:
obtaining a measurement of a calibration structure mounted on the first optical metrology tool using the first optical metrology tool;
generating a drift function based on the obtained measurement of the calibration structure; and
generating the first adjusted diffraction signal by adjusting the first measured diffraction signal using the drift function.

17. A system of matching optical metrology tool, the system comprising:
a computer-readable storage medium configured to store:
a first spectra-shift offset, wherein the first spectra-shift offset was generated based on the difference between a first set of measured diffraction signals measured using a first optical metrology tool and a second set of measured diffraction signals measured using a second optical metrology tool; and
a first noise weighting function for the first optical metrology tool, wherein the first noise weighting function was generated based on measured diffraction signals measured using the first optical metrology tool; and
a processor configured to:
obtain a first measured diffraction signal measured using the first optical metrology tool;
generate a first adjusted diffraction signal by adjusting the first measured diffraction signal using the first spectra-shift offset and the first noise weighting function; and
store the first adjusted diffraction signal.

18. The system of claim 17,
wherein the computer-readable storage medium is further configured to store:
a second spectra-shift offset, wherein the second spectra-shift offset was generated based on the difference between a third set of measured diffraction signals measured using a third optical metrology tool and the second set of measured diffraction signals measured using the second optical metrology tool; and
a second noise weighting function for the third optical metrology tool, wherein the second noise weighting function was generated based on measured diffraction signals measured using the third optical metrology tool; and
wherein the processor is further configured to:
obtain a second measured diffraction signal measured using the third optical metrology tool; and
generate a second adjusted diffraction signal by adjusting the second measured diffraction signal using the second spectra-shift offset and the second noise weighting function.

19. The system of claim 17, wherein the computer-readable storage medium is further configured to store a drift function for the first optical metrology tool, wherein the drift function was generated based on obtained measurements of a calibration structure mounted on the first optical metrology tool using the first optical metrology tool at different times, and wherein the processor is further configured to generate the first adjusted diffraction signal by adjusting the first measured diffraction signal using the drift function.

20. A method of matching optical metrology tools, the method comprising:
obtaining a first set of measured diffraction signals, wherein the first set of measured diffraction signals was measured using a first optical metrology tool;
obtaining a second set of measured diffraction signals, wherein the second set of measured diffraction signals was measured using a second optical metrology tool;
generating a first spectra-shift offset based on the difference between the first set of measured diffraction signals and the second set of measured diffraction signals;
generating a first noise weighting function for the first optical metrology tool based on measured diffraction signals measured using the first optical metrology tool; and
storing the first spectra-shift offset and the first noise weighting function in a computer-readable storage medium.

21. The method of claim 20, further comprising:
obtaining a first measured diffraction signal measured using the first optical metrology tool;
retrieving the first spectra-shift offset and the first noise weighting function from the computer-readable storage medium; and generating a first adjusted diffraction signal by adjusting the first measured diffraction signal using the retrieved first spectra-shift offset and the first noise weighting function.

22. The method of claim 20, further comprising:
obtaining a third set of measured diffraction signals, wherein the third set of measured diffraction signals was measured using a third optical metrology tool;
generating a second spectra-shift offset based on the difference between the third set of measured diffraction signals and the second set of measured diffraction signals;
generating a second noise weighting function for the third optical metrology tool based on measured diffraction signals measured using the third optical metrology tool; and
storing the second spectra-shift offset and the second noise weighting function in the computer-readable storage medium.

23. The method of claim 22, further comprising:
obtaining a second measured diffraction signal measured using the third optical metrology tool;
retrieving the second spectra-shift offset and the second noise weighting function from the computer-readable storage medium; and
generating a second adjusted diffraction signal by adjusting the second measured diffraction signal using the retrieved second spectra-shift offset and the second noise weighting function.

24. The method of claim 20, further comprising:
obtaining a measurement of a calibration structure mounted on the first optical metrology tool using the first optical metrology tool;
generating a drift function based on the obtained measurement of the calibration structure; and
storing the drift function in the computer-readable storage medium.

25. The method of claim 24, further comprising:
retrieving the drift function; and
generating the first adjusted diffraction signal by adjusting the first measured diffraction signal using the retrieved drift function.

26. A computer-readable storage medium having computer executable instructions for matching optical metrology tools, comprising instructions for:
obtaining a first set of measured diffraction signals, wherein the first set of measured diffraction signals was measured using a first optical metrology tool;
obtaining a second set of measured diffraction signals, wherein the second set of measured diffraction signals was measured using a second optical metrology tool;
generating a first spectra-shift offset based on the difference between the first set of measured diffraction signals and the second set of measured diffraction signals;
generating a first noise weighting function for the first optical metrology tool based on measured diffraction signals measured using the first optical metrology tool; and
storing the first spectra-shift offset and the first noise weighting function in a computer-readable storage medium.

27. The computer-readable storage medium of claim 26, further comprising instructions for:
obtaining a first measured diffraction signal measured using the first optical metrology tool;
retrieving the first spectra-shift offset and the first noise weighting function from the computer-readable storage medium; and
generating a first adjusted diffraction signal by adjusting the first measured diffraction signal using the retrieved first spectra-shift offset and the first noise weighting function.

28. The computer-readable storage medium of claim 26, further comprising instructions for:
obtaining a third set of measured diffraction signals, wherein the third set of measured diffraction signals was measured using a third optical metrology tool;
generating a second spectra-shift offset based on the difference between the third set of measured diffraction signals and the second set of measured diffraction signals;
generating a second noise weighting function for the third optical metrology tool based on measured diffraction signals measured using the third optical metrology tool; and
storing the second spectra-shift offset and the second noise weighting function in the computer-readable storage medium.

29. The computer-readable storage medium of claim 28, further comprising instructions for:
obtaining a second measured diffraction signal measured using the third optical metrology tool;
retrieving the second spectra-shift offset and the second noise weighting function from the computer-readable storage medium; and
generating a second adjusted diffraction signal by adjusting the second measured diffraction signal using the retrieved second spectra-shift offset and the second noise weighting function.

30. The computer-readable storage medium of claim 26, further comprising instructions for:
obtaining a measurement of a calibration structure mounted on the first optical metrology tool using the first optical metrology tool;
generating a drift function based on the obtained measurement of the calibration structure; and
storing the drift function in the computer-readable storage medium.

31. The computer-readable storage medium of claim 30, further comprising instructions for:
retrieving the drift function; and
generating the first adjusted diffraction signal by adjusting the first measured diffraction signal using the retrieved drift function.

32. A system for matching optical metrology tools, the system comprising:
a first optical metrology tool configured to measure a first set of measured diffraction signals;
a second optical metrology tool configured to measure a second set of measured diffraction signals;
a processor module configured to:
generate a first spectra-shift offset based on the difference between the first set of measured diffraction signals and the second set of measured diffraction signals;
generate a first noise weighting function for the first optical metrology tool based on measured diffraction signals measured using the first optical metrology tool; and
store the first spectra-shift offset and the first noise weighting function in a computer-readable storage medium.

33. A method of matching optical metrology tools, the method comprising:
- obtaining a first measured diffraction signal, wherein the first measured diffraction signal was measured using a first optical metrology tool;
- obtaining a first spectra-shift offset for the first optical metrology tool, wherein the first spectra-shift offset was generated based on the difference between a first set of measured diffraction signals measured using the first optical metrology tool and a second set of measured diffraction signals measured using a second optical metrology tool;
- obtaining a first noise weighting function for the first optical metrology tool, wherein the first noise weighting function was generated based on measured diffraction signals measured using the first optical metrology tool;
- generating a first adjusted diffraction signal by adjusting the first measured diffraction signal using the first spectra-shift offset and the first noise weighting function; and
- storing the first adjusted diffraction signal.

34. The method of claim 33, further comprising:
- obtaining a second measured diffraction signal, wherein the second measured diffraction signal was measured using a third optical metrology tool;
- obtaining a second spectra-shift offset for the third optical metrology tool, wherein the second spectra-shift offset was generated based on the difference between a third set of measured diffraction signals measured using the third optical metrology tool and the second set of measured diffraction signals measured using the second optical metrology tool;
- obtaining a second noise weighting function for the third optical metrology tool based on measured diffraction signals measured using the third optical metrology tool; and
- generating a second adjusted diffraction signal by adjusting the second measured diffraction signal using the second spectra-shift offset and the second noise weighting function.

35. A computer-readable storage medium having computer executable instructions for matching optical metrology tools, comprising instructions for:
- obtaining a first measured diffraction signal, wherein the first measured diffraction signal was measured using a first optical metrology tool;
- obtaining a first spectra-shift offset for the first optical metrology tool, wherein the first spectra-shift offset was generated based on the difference between a first set of measured diffraction signals measured using the first optical metrology tool and a second set of measured diffraction signals measured using a second optical metrology tool;
- obtaining a first noise weighting function for the first optical metrology tool, wherein the first noise weighting function was generated based on measured diffraction signals measured using the first optical metrology tool;
- generating a first adjusted diffraction signal by adjusting the first measured diffraction signal using the first spectra-shift offset and the first noise weighting function; and
- storing the first adjusted diffraction signal.

36. The computer-readable storage medium of claim 35, further comprising instructions for:
- obtaining a second measured diffraction signal, wherein the second measured diffraction signal was measured using a third optical metrology tool;
- obtaining a second spectra-shift offset for the third optical metrology tool, wherein the second spectra-shift offset was generated based on the difference between a third set of measured diffraction signals measured using the third optical metrology tool and the second set of measured diffraction signals measured using the second optical metrology tool;
- obtaining a second noise weighting function for the third optical metrology tool based on measured diffraction signals measured using the third optical metrology tool; and
- generating a second adjusted diffraction signal by adjusting the second measured diffraction signal using the second spectra-shift offset and the second noise weighting function.

37. A system for matching optical metrology tools, the system comprising:
- a first optical metrology tool configured to measure a first measured diffraction signal; and
- a processor module configured to:
  - obtain a first spectra-shift offset for the first optical metrology tool, wherein the first spectra-shift offset was generated based on the difference between a first set of measured diffraction signals measured using the first optical metrology tool and a second set of measured diffraction signals measured using a second optical metrology tool;
  - obtain a first noise weighting function for the first optical metrology tool, wherein the first noise weighting function was generated based on measured diffraction signals measured using the first optical metrology tool;
  - generate a first adjusted diffraction signal by adjusting the first measured diffraction signal using the first spectra-shift offset and the first noise weighting function; and
  - store the first adjusted diffraction signal.

* * * * *